(12) United States Patent
Shah et al.

(10) Patent No.: US 12,151,103 B2
(45) Date of Patent: Nov. 26, 2024

(54) SYSTEMS AND METHODS FOR ARTIFICIAL SIGHT PROSTHETICS

(71) Applicant: The Board of Trustees of the Leland Stanford Junior University, Stanford, CA (US)

(72) Inventors: Nishal Pradeepkumar Shah, Stanford, CA (US); Eduardo Jose Chichilnisky, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 446 days.

(21) Appl. No.: 17/441,261

(22) PCT Filed: Mar. 23, 2020

(86) PCT No.: PCT/US2020/024298
§ 371 (c)(1),
(2) Date: Sep. 20, 2021

(87) PCT Pub. No.: WO2020/191408
PCT Pub. Date: Sep. 24, 2020

(65) Prior Publication Data
US 2022/0168571 A1 Jun. 2, 2022

Related U.S. Application Data

(60) Provisional application No. 62/821,763, filed on Mar. 21, 2019.

(51) Int. Cl.
*A61N 1/36* (2006.01)
*A61N 1/05* (2006.01)
(Continued)

(52) U.S. Cl.
CPC ....... *A61N 1/36046* (2013.01); *A61N 1/0543* (2013.01); *A61N 1/08* (2013.01); *A61N 1/37235* (2013.01); *A61N 1/025* (2013.01)

(58) Field of Classification Search
CPC .... A61N 1/36046; A61N 1/0543; A61N 1/08; A61N 1/37235; A61N 1/025
See application file for complete search history.

(56) References Cited

U.S. PATENT DOCUMENTS

2002/0010496 A1* 1/2002 Greenberg ................ G06T 3/40
607/54
2004/0102843 A1* 5/2004 Yagi ...................... A61F 2/1602
623/4.1
(Continued)

FOREIGN PATENT DOCUMENTS

EP 3941572 A1 1/2022
WO 2020191408 A1 9/2020

OTHER PUBLICATIONS

Extended European Search Report for European Application No. 20773702.4, Search completed Oct. 12, 2022, Mailed Oct. 20, 2022, 8 Pgs.
(Continued)

*Primary Examiner* — Eugene T Wu
(74) *Attorney, Agent, or Firm* — KPPB LLP (57) ABSTRACT

Systems and methods for artificial sight in accordance with embodiments of the invention are illustrated. One embodiment includes a retinal prosthesis system including an external controller, a scene imager, an eye imager, an implanted controller, and a stimulation interface in communication with the implanted controller, where the stimulation interface is positioned to stimulate a plurality of retinal ganglion cells (RGCs) of the eye, where the external controller is configured to obtain image data describing a scene from the scene imager, obtain eye position data from the eye
(Continued)

imager, determine a field of view (FOV) in the scene based on the eye position data; where the implanted controller is configured to obtain the FOV from the external controller, continuously select stimulation pulses from a dictionary based on the FOV, and stimulate the plurality of RGCs using the stimulation interface in accordance with the selected stimulation pulses.

20 Claims, 8 Drawing Sheets

(51) Int. Cl.
    *A61N 1/08*         (2006.01)
    *A61N 1/372*       (2006.01)
    *A61N 1/02*         (2006.01)

(56) References Cited

U.S. PATENT DOCUMENTS

| | | | |
|---|---|---|---|
| 2006/0058857 A1 | 3/2006 | Tano et al. | |
| 2010/0094382 A1* | 4/2010 | Pezaris | A61N 1/372 607/54 |
| 2012/0143080 A1 | 6/2012 | Greenberg et al. | |
| 2012/0221076 A1* | 8/2012 | Sharpee | A61N 1/36046 607/54 |
| 2014/0236260 A1* | 8/2014 | McDermott | A61N 1/36046 607/54 |
| 2019/0232051 A1* | 8/2019 | Gross | A61N 1/36046 |

OTHER PUBLICATIONS

International Preliminary Report on Patentability for International Application PCT/US2020/024298, issued Sep. 16, 2021, Mailed Sep. 30, 2021, 7 Pgs.
International Search Report and Written Opinion for International Application No. PCT/US2020/024298, search completed on May 29, 2020, Mailed on Jun. 19, 2020, 12 Pgs.
"Argus II Retinal Prosthesis System Surgeon Manual", Second Sign Medical Products, Inc., 2013, 380 pgs.
Aprile et al., "Adaptive Learning-Based Compressive Sampling for Low-power Wireless Implants", IEEE Transactions on Circuits and Systems I Regular Papers, vol. 65, 2018, pp. 3929-3941.
Asher et al., "Image Processing for a High-Resolution Optoelectronic Retinal Prosthesis", IEEE Transactions on Biomedical Engineering, Jun. 2007, vol. 54, Issue 6, pp. 993-1004.
Ayton et al., "First-in-Human Trial of a Novel Suprachoroidal Retinal Prothesis", PLOS One, Dec. 18, 2014, 26 pgs.
Beyeler et al., "Learning to see again: biological constraints on cortical plasticity and the implications for sight restoration technologies", Journal of Neural Engineering, vol. 14, 2017, 19 pgs, doi: 10.1088/1741-2552/aa795e.
Boinagrov et al., "Strength-duration relationship for extracellular neural stimulation: numerical and analytical models", Journal of Neurophysiology, vol. 104, 2010, pp. 2236-2248, doi: 10.1152/jn.00343.2010.
Butterwick et al., "Tissue damage by pulsed electrical stimulation", IEEE Transactions on Biomedical Engineering, vol. 54, No. 12, Dec. 2007, pp. 2261-2267.
Carlson et al., "Continuing progress of spike sorting in the era of big data", Current Opinion in Neurobiology, vol. 55, Apr. 2019, pp. 90-96.
Caspi et al., "Feasibility study of a retinal prosthesis: spatial vision with a 16-electrode implant", Archives of Ophthalmology, vol. 127, No. 4, Apr. 2009, pp. 398-401.
Chader et al., "Artificial vision: needs, functioning, and testing of a retinal electronic prosthesis", Progress in Brain Research, vol. 175, 2009, pp. 317-332.
Chestek et al., "Long-term stability of neural prosthetic control signals from silicon cortical arrays in rhesus macaque motor cortex", Journal of neural engineering, 8(4):045005, Jul. 2011.
Chichilnisky et al., "Functional asymmetries in ON and OFF ganglion cells of primate retina", The Journal of Neuroscience, vol. 22, No. 7, Apr. 1, 2002, pp. 2737-2747.
Christie et al., "Comparison of spike sorting and thresholding of voltage waveforms for intracortical brain-machine interface performance", Journal of Neural Engineering, vol. 12, No. 1, Feb. 2015, doi: 10.1088/1741-2560/12/1/016009.
Chuang et al., "Retinal implants: a systematic review", The British Journal of Ophthalmology, vol. 98, 2008, pp. 852-856.
Chung et al., "A Fully Automated Approach to Spike Sorting", Neuron, vol. 95, Issue 6, Sep. 2017, pp. 1381-1394.
Cogan, "Neural stimulation and recording electrodes", Annual Review of Biomedical Engineering, 2008, vol. 10, pp. 275-309, first published online Apr. 22, 2008, doi: 10.1146/annurev.bioeng.10.061807.160518.
Dayan et al., "Theoretical neuroscience: computational and mathematical modeling of neural systems", MIT Press, 2001, 476 pgs.
De Balthasar et al., "Factors affecting perceptual thresholds in epiretinal prostheses", Investigative Ophthalmology and Visual Science, vol. 49, 2008, pp. 2303-2314.
Fan et al., "Epiretinal stimulation with local returns enhances selectivity at cellular resolution", The Journal of Neural Engineering, vol. 16, No. 2, Apr. 2019, 20 pgs.
Field et al., "Functional connectivity in the retina at the resolution of photoreceptors", Nature, vol. 467, No. 7316, Oct. 7, 2010, pp. 673-677.
Fohlmeister et al., "Modeling the repetitive firing of retinal ganglion cells", Brain Research, vol. 510, Issue 2, Mar. 5, 1990, pp. 343-345.
Fraser et al., "Control of a brain—computer interface without spike sorting", Journal of Neural Engineering, vol. 6, No. 5, Oct. 2009, doi: 10.1088/1741-2560/6/5/055004.
Frechette et al., "Fidelity of the Ensemble Code for Visual Motion in Primate Retina", Journal of Neurophysiology, vol. 94, No. 1, Jul. 2005, pp. 119-135, doi:10.1152/jn.01175.2004.
Goetz et al., "Electronic Approaches to Restoration of Sight", Reports on progress in physics, institute of physics publishing, Bristol, GB, Aug. 9, 2016, vol. 79, No. 9, p. 96701, XP020307763, ISSN: 0034-4885, DOI: 10.1088/0034-4885/79/9/096701.
Gollisch et al., "Eye smarter than scientists believed: neural computations in circuits of the retina", Neuron, vol. 65, No. 2, Jan. 2010, pp. 150-164.
Grifantini, , "Aiding the Eye, Watching the Brain: James Weiland, IEEE Fellow, explores the unique challenges of retinal prostheses.", IEEE Pulse, vol. 8, pp. 39-41.
Grosberg et al., "Activation of ganglion cells and axon bundles using epiretinal electrical stimulation", Journal Neurophysiology, vol. 118, No. 3, Sep. 1, 2017, pp. 1457-1471, doi: 10.1152/jn.00750.2016.
Halupka et al., "Prediction of cortical responses to simultaneous electrical stimulation of the retina", Journal of Neural Engineering, vol. 14, No. 1, Nov. 30, 2016, 17 pgs.
Horsager et al., "Predicting visual sensitivity in retinal prosthesis patients", Investigative Ophthalmology and Visual Science, vol. 50, 2009, pp. 1483-1491.
Humayun et al., "The Bionic Eye: A Quarter Century of Retinal Prosthesis Research and Development", Ophthalmology, vol. 123, 2016, pp. S89-S97.
Jensen et al., "Thresholds for activation of rabbit retinal ganglion cells with an ultrafine, extracellular microelectrode", Investigative. Ophthalmology & Visual Science, vol. 44, No. 8, Aug. 2003, pp. 3533-3543, doi: 10.1167/iovs.02-1041.
Jepson et al., "Focal electrical stimulation of major ganglion cell types in the primate retina for the design of visual prostheses", Journal of Neuroscience, vol. 33, No. 17, Apr. 24, 2013, pp. 7194-7205.
Jepson et al., "High-fidelity reproduction of spatiotemporal visual signals for retinal prosthesis", Neuron, vol. 83, Jul. 2014, pp. 87-92.
Jepson et al., "Spatially Patterned Electrical Stimulation to Enhance Resolution of Retinal Prostheses", The Journal of Neuroscience, vol. 34, No. 14, Apr. 2014, pp. 4871-4881.

(56) References Cited

OTHER PUBLICATIONS

John et al., "Suprachoroidal electrical stimulation: Effects of stimulus pulse parameters on visual cortical responses", Bionics Institute, Accepted for publication in: Journal of Neural Engineering, vol. 10, No. 5, Aug. 8, 2013, 36 pgs.

Jung et al., "Active confocal imaging for visual prostheses", Vision Research, vol. 111, 2014, pp. 182-196.

Karkare et al., "A 75-µW, 16-Channel Neural Spike-Sorting Processor With Unsupervised Clustering.", IEEE Journal of Solid-State Circuits, vol. 48, 2011, pp. 2230-2238.

Lebedev et al., "Brain-Machine Interfaces: From Basic Science to Neuroprostheses and Neurorehabilitation", Physiological Review, vol. 97, No. 2, Mar. 8, 2017, pp. 767-837, doi: 10.1152/physrev. 00027.2016.

Li et al., "Sums of Spike Waveform Features for Motor Decoding", Frontiers in Neuroscience, vol. 11, No. 406, Jul. 18, 2017, doi: 10.3389/fnins.2017.00406.

Litke et al., "What Does the Eye Tell the Brain ?: Development of a System for the Large-Scale Recording of Retinal Output Activity", IEEE Transaction Nuclear Science, vol. 51, No. 4, Aug. 2004, pp. 1434-1440, DOI: 10.1109/TNS.2004.832706.

Lorach et al., "Photovoltaic restoration of sight with high visual acuity", Nature Medicine, vol. 21, 2015, pp. 476-482.

Majidzadeh et al., "A 16-channel, 359 µW, parallel neural recording system using Walsh-Hadamard coding", Proceedings of the IEEE 2013 Custom Integrated Circuits Conference, 2013, pp. 1-4.

Marblestone et al., "Physical Principles for Scalable Neural Recording", Frontiers in Computational Neuroscience, vol. 7, No. 137, 2013, 49 pgs.

Maturana et al., "A Simple and Accurate Model to Predict Responses to Multi-electrode Stimulation in the Retina", PLOS Computational Biology, Apr. 1, 2016, 26 pgs.

Meffin et al., "Modeling extracellular electrical stimulation: I. Derivation and interpretation of neurite equations", Journal of Neural Engineering, vol. 9, 2012, 19 pgs.

Merrill et al., "Electrical stimulation of excitable tissue: design of efficacious and safe protocols", Journal of Neuroscience Methods, vol. 141, 2005, pp. 171-198.

Muratore et al., "A Data-Compressive Wired-OR Readout for Massively Parallel Neural Recording", IEEE Transactions on Biomedical Circuits and Systems, 2019, doi: 10.1109/TBCAS.2019. 2935468.

Nanduri et al., "Retinal prosthesis phosphene shape analysis", 2008 30th Annual International Conference of the IEEE Engineering in Medicine and Biology Society, 2008, pp. 1785-1788.

Nayagam et al., "Chronic Electrical Stimulation with a Suprachoroidal Retinal Prosthesis: A Preclinical Safety and Efficacy Study", PLOS One, vol. 9, No. 5, May 2014, 21 pgs.

Okazawa et al., "A Time-Domain Analog Spatial Compressed Sensing Encoder for MultiChannel Neural Recording", Sensors, vol. 18, No. 1, Jan. 2018, 21 pgs.

Pagin et al., "A Neural Data Lossless Compression Scheme Based on Spatial and Temporal Prediction", IEEE Biomedical Circuits and Systems Conference, Oct. 2017.

Reddy et al., "Bionic Eye: A Glance at the Argus II retinal prosthesis", MedCrave, Advances in Ophthalmology & Visual System, vol. 2, No. 3, 2015, 5 pgs.

Rey et al., "Past, present and future of spike sorting techniques.", Brain Research Bulletin, vol. 119, 2015, pp. 106-117.

Rhoades et al., "Unusual Physiological Properties of Smooth Monostratified Ganglion Cell Types in Primate Retina.", Neuron, vol. 103, No. 4, Aug. 21, 2019, pp. 658-672.e6.

Richard et al., "Recognizing retinal ganglion cells in the dark. In: Advances in Neural Information Processing Systems", Stanford Medicine, 2015, pp. 2476-2484.

Sekirnjak et al., "High-resolution electrical stimulation of primate retina for epiretinal implant design", Journal of Neuroscience, vol. 28, No. 17, Apr. 23, 2008, pp. 4446-4456.

Shah et al., "Efficient characterization of electrically evoked responses for neural interfaces", Neural Information Processing Systems (NeurIPS), 2019.

Shah et al., "Optimization of Electrical Stimulation for a High-Fidelity Artificial Retina", 2019 9th International IEEE/EMBS Conference on Neural Engineering (NER), IEEE, Mar. 20, 2019, pp. 714-718, XP033551652, DOI: 10.1109/NER.2019.8716987.

Sharma et al., "Acquisition of Neural Action Potentials Using Rapid Multiplexing Directly at the Electrodes", Micromachines, vol. 9, No. 477, 2018, doi: 10.3390/mi9100477.

Shepherd et al., "Visual Prostheses for the Blind", Trends in Biotechnology, vol. 31, No. 10, 2013, pp. 562-571.

Slutzky, , "Brain-Machine Interfaces: Powerful Tools for Clinical Treatment and Neuroscientific Investigations", Neuroscientist, Author manuscript available in PMC Apr. 1, 2020, published in final edited form as Neuroscientist, vol. 25, No. 3, Apr. 2019, pp. 139-154, published online May 17, 2018, doi: 10.1177/1073858418775355.

Trautmann et al., "Accurate Estimation of Neural Population Dynamics Without Spike Sorting", Neuron, vol. 103, No. 2, Jul. 17, 2019, 42 pgs.

Tsai et al., "Statistically Reconstructed Multiplexing for Very Dense, High-Channel-Count Acquisition Systems", IEEE Transactions on Biomedical Circuits and Systems, vol. 12, 2018, pp. 13-23.

Villalobos et al., "A wide-field suprachoroidal retinal prosthesis is stable and well tolerated following chronic implantation", Investagative Ophthalmology & Visual Science, vol. 54, No. 5, May 2013, pp. 3751-3762.

Wang et al., "Fast and Robust Object DetectionUsing Asymmetric Totally-corrective Boosting", IEEE Transaction on Neural Networks, 2011, 15 pgs.

Wilke et al., "Spatial Resolution and Perception of Patterns Mediated by a Subretinal 16-Electrode Array in Patients Blinded by Hereditary Retinal Dystrophies", Investigative Ophthalmology & Visual Science, vol. 52, No. 8, Jul. 2011, 9 pgs.

Wu et al., "Deep compressive autoencoder for action potential compression in large-scale neural recording", Journal of Neural Engineering, vol. 15, No. 6, Dec. 2018, 20 pgs.

YH-L et al., "A review and update on the current status of retinal prostheses (bionic eye)", British Medical Bulletin, vol. 109, 2014, pp. 31-44.

Zhou et al., "Toward true closed-loop neuromodulation: artifact-free recording during stimulation", Current Opinion in Neurobiology, vol. 50, 2018, pp. 119-127.

Zrenner et al., "Fighting blindness with microelectronics", Science Translational Medicine, vol. 5, No. 210, Nov. 2013.

Zrenner et al., "Subretinal electronic chips allow blind patients to read letters and combine them to words", Proceedings of the Royal Society B: Biological Sciences, vol. 278, 2011, pp. 1489-1497.

"The BVT Bionic Eye", Bionic Vision Technologies, 2018, 2 pgs.

Beauchamp et al., "Dynamic Stimulation of Visual Cortex Produces Form Vision in Sighted and Blind Humans", Cell, vol. 181, No. 4, May 14, 2020, pp. 774-783.e5.

Roska et al., "The retina dissects the visual scene into distinct features", The New Visual Neurosciences, 2014, pp. 163-182.

Shah et al., "Greedy dictionary-based stimulation for optimization of epiretinal prosthesis", TEATC, Sep. 2017.

Shah et al., "Real Time Optimization of Visual Coding for Artificial Retina", Stanford University, Mar. 5, 2018.

* cited by examiner

FIG. 8

SYSTEMS AND METHODS FOR ARTIFICIAL SIGHT PROSTHETICS

CROSS-REFERENCE TO RELATED APPLICATIONS

The current application is a national stage of PCT Application No. PCT/US2020/024298 entitled "Systems and Methods for Artificial Sight Prosthetics" filed Mar. 23, 2020, which claims the benefit of and priority under 35 U.S.C. § 119(e) to U.S. Provisional Patent Application No. 62/821,763 entitled "Systems and Methods for Dictionary-Based Artificial Sight Prosthetics" filed Mar. 21, 2019 the disclosures of which are hereby incorporated by reference in their entireties for all purposes.

STATEMENT OF FEDERALLY SPONSORED RESEARCH

This invention was made with Government support under contract 1430348 awarded by the National Science Foundation and under contract EY021271 awarded by the National Institutes of Health. The Government has certain rights in the invention.

FIELD OF THE INVENTION

The present invention generally relates artificial sight, and, more specifically, to artificial retina vision restoration apparatuses using dictionary-based image reconstruction and temporal dithering.

BACKGROUND

The eye is a highly complex biological organ that grants an organism the ability to receive visual information by converting light into electrical impulses (spikes) in neurons. In the human eye, light passes through the cornea, then through a dilated pupil, and then through an adjustable lens that can be used to manipulate focus. The focused light travels through a cavity filled with vitreous humor until it hits photoreceptors, the photosensitive cells of the retinas (i.e. rods and cones). Depending on the amplitude and wavelength of the light, the photoreceptors generate and transmit electrical signals to the brain via retinal ganglion cells, where they are processed to produce the sense of "sight." The inability to see is called blindness. Blindness may result from any number of different sources including, but not limited to, damage to the photoreceptors, the eye, the optic nerve, brain damage, and/or other forms of damage to the structures associated with sight.

Digital cameras are image-forming optical systems that are capable of receiving light and generating an image of a scene. Cameras include at least one lens and a photosensitive sensor. Computational processing techniques are used to resolve the received light into an image.

SUMMARY OF THE INVENTION

Systems and methods for artificial sight in accordance with embodiments of the invention are illustrated. One embodiment includes a retinal prosthesis system including an external controller, a scene imager in communication with the external controller, an eye imager in communication with the external controller, an implanted controller in communication with the external controller via a first communication channel, and a stimulation interface in communication with the implanted controller via a second communication channel, where the stimulation interface is positioned to stimulate a plurality of retinal ganglion cells (RGCs) of the eye, and the stimulation interface comprises a dense electrode grid, where the external controller is configured to obtain image data describing a scene from the scene imager, obtain eye position data from the eye imager, determine a field of view (FOV) in the scene based on the eye position data; and transmit the FOV to the implanted controller, where the implanted controller is configured to obtain the FOV from the external controller, continuously select stimulation pulses from a dictionary based on the FOV, and stimulate the plurality of RGCs using the stimulation interface in accordance with the selected stimulation pulses.

In another embodiment, the stimulation of the RGCs is performed at between 10 kHz to 100 kHz.

In a further embodiment, the dictionary is a master dictionary; and the external controller is further configured to transmit the master dictionary to the implanted controller.

In still another embodiment, to compile the master dictionary, the external controller is configured to, stimulate the plurality of RGCs using the stimulation interface via the implanted controller, record responses of the plurality of RGCs based on the stimulation using the stimulation interface, via the implanted controller, and generate a set of dictionary elements indicating neural activity in response to specific stimulation provided by the stimulation interface.

In a still further embodiment, the master dictionary is a reduced master dictionary.

In yet another embodiment, the dictionary is a FOV dictionary, wherein to compile the FOV dictionary, the external controller is configured to select elements from a master dictionary which are most relevant to the FOV, and the external controller is further configured to transmit the FOV dictionary to the implanted controller.

In a yet further embodiment, to select elements from the master dictionary, the external controller is configured to calculate a vector $q^*=\max f(S,Dq)$; with $q \geq 0$; $\Sigma_i q_i \leq B$, and selecting dictionary elements of $q^*$ which are non-zero.

In another additional embodiment, the internal controller is further configured to use a precompiled dictionary in an interim period between receiving the FOV and receiving the FOV dictionary.

In a further additional embodiment, the first communication channel is a wireless communication channel utilizing a near-field magnetic communication technology.

In another embodiment again, the first communication channel is a wireless communication channel utilizing a radio frequency communication technology conforming to the Bluetooth standard.

In a further embodiment again, the second communication channel is a wired communication channel configured to power the dense electrode grid.

In still yet another embodiment, the second communication channel is a wireless communication channel.

In a still yet further embodiment, stimulation of the plurality of RGCs occurs with sufficient speed to trigger the temporal dithering effect.

In still another additional embodiment, to select stimulation pulses from the dictionary and the FOV, the implanted controller is further configured to utilize a greedy algorithm.

In a still further additional embodiment, to select stimulation pulses from the dictionary and the FOV, the implanted controller is further configured to utilize a dynamic programming algorithm.

In still another embodiment again, the implanted controller is configured to be implanted in the episcleral layer of an eye.

In a still further embodiment again, the implanted controller is incorporated into a contact lens.

In yet another additional embodiment, a method for providing artificial sight, including obtaining image data describing a scene from a scene imager, obtaining eye position data from an eye imager, determining a field of view (FOV) in the scene based on the eye position data using a retinal prosthesis, continuously selecting stimulation pulses from a dictionary and the FOV using the retinal prosthesis, and stimulating a plurality of retinal ganglion cells using a stimulation interface of the retinal prosthesis in accordance with the selected stimulation pulses.

In a yet further additional embodiment, the dictionary is a FOV dictionary which is compiled by selecting elements from a master dictionary which are most relevant to the FOV.

In yet another embodiment again, selecting stimulation pulses from the dictionary based on the FOV is achieved using a greedy algorithm.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Sight is one of the most important senses available to a person, if not the most important, as vision is the primary way in which humans perceive their environment. For example, when communicating with another person, a significant amount of information is obtained via-nonverbal communication (e.g. body language). Indeed, sight is valuable for nearly every human activity. Systems and methods described herein are capable of granting or restoring sight to individuals that have at least partially intact retinas but are otherwise partially or completely blind.

Retinal prosthetics are devices that use electrodes to stimulate the retinal ganglion cells in a specific manner to evoke visual perception of the surrounding environment in a blind patient. In order to create high quality artificial vision, retinal prosthetics need to accurately reproduce the diverse and specific firing pattern of approximately 20 different retinal ganglion cell (RGC) types, each conveying a distinct visual feature to the brain. However, a single stimulation electrode can simultaneously activate multiple adjacent cells, regardless of their type, making it difficult to simulate the asynchronous neural code employed by the human physiology. Systems and methods described herein can address these problems by identifying the RGCs of different types in a patient's retina, measuring their responses to electrical stimulation, and using this information to optimize the artificial visual signal by real-time control of stimulation using personalized dictionaries and algorithms.

Further, while modern retinal prosthetic systems perform visual signal processing on external control devices, the lag time for sending stimulation information from outside the body to inside the body can cause significant degradation in sight quality, particularly because normal vision is closely locked to rapid eye movements which may disrupt wireless communication between implanted and external devices. However, computational processing generates significant amounts of heat, and excessive amounts of heat can damage the structure of the eye, making it difficult to perform significant computations in an implanted device. Systems and methods described herein are capable of assigning processing tasks across external and implanted controllers in order to optimize processing and communication speeds to decrease lag time and heat load applied to the eye and retina. In numerous embodiments, implanted components do not require more than 1 milliwatt per millimeter squared on the surface of the retina (1 mW/mm$^2$).

While current artificial retina systems have achieved limited success with enabling patients to generally navigate some areas via artificial sight, higher fidelities have not been achieved. Systems and methods described herein attempt to resolve these problems using efficient visual stimulation strategies based on tuning the device to the neural circuitry of the retina and using dictionary-based approaches for rapid computation. Turning now to the drawings, systems for artificial sight are discussed below.

Artificial Sight Systems

Systems for artificial sight are retinal prosthetic systems that can generate dictionaries for RGC stimulation. In numerous embodiments, systems for artificial sight utilize both implanted and external controllers to increase the overall efficiency of the system and increase visual fidelity. Systems for artificial sight can balance the heat generated by processing with the need for rapid processing and rapid communication between components.

Figure 1:
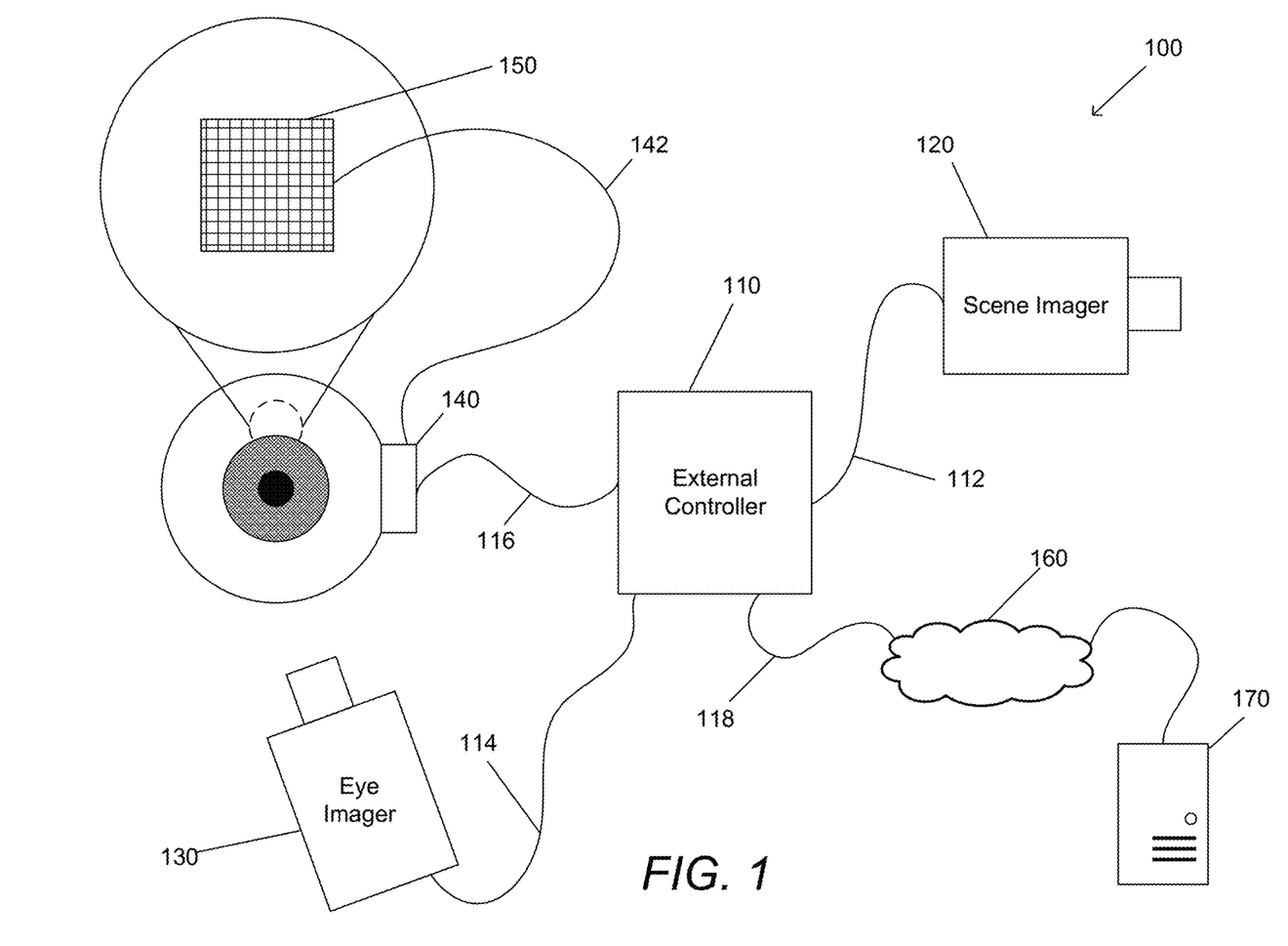
FIG. 1 conceptually illustrates an artificial sight system in accordance with an embodiment of the invention.

Turning now to FIG. 1, a system for artificial sight in accordance with an embodiment of the invention is illustrated. System 100 includes an external controller 110. In many embodiments, external controllers carry processing circuitry necessary to perform various artificial sight processes. In numerous embodiments, external controllers are capable of receiving image information describing a scene from a scene imager, eye position information from an eye imager. In many embodiments, the eye imager is capable of measuring and/or tracking the pupil and/or iris of a patient, fiduciary marks on a contact lens, blood vessels within the eye, the stimulation interface and/or the implanted controller in order to accurately measure the eye position information. External controllers can use image information and eye position information to compute field of view in a visual scene and compile dictionaries based on the received image information and eye position information. External controllers can transmit and receive data via at least one input/output interface. External controller input/output interfaces can transmit information across at least one communication channel. Channels can be either wired or wireless. External controllers are capable of utilizing at least two channels, where one channel is used to communicate with an input/output interface of an implanted controller, and where one channel is used to communicate with imagers. In some embodiments, external controllers are capable of communicating with configuration systems via a third channel. However, in some embodiments, communication to and from configuration systems can be accomplished via the same channel as used by the imagers. In a variety of embodiments, the external controller uses a wireless communication channel for exchanging data with the implanted controller, and a wired communication channel for exchanging data with the imagers. The wireless communication channel can be any number of different wireless channels, such as, but not limited to, radio communication (e.g. via the Bluetooth standard, or any other wireless communication method), magnetic communication methods (e.g. near-field magnetic induction communication), ultrasound communication, optical communication, and/or any other low power communication method that is safely usable in conjunction with an implanted controller adjacent to the human eye. In numerous embodiments, the external controller is further capable of transmitting power wirelessly to an implanted controller.

External controller 110 is connected to a scene imager 120 via a communication channel 112. As discussed above, communication channel 112 can be wired or wireless. Communication channel 112 is capable of relatively high-bandwidth communications to enable external controller 110 to receive images of the scene at a high frame rate of approximately 10-240 Hz. Scene imagers can be any image sensor capable of capturing images of an external environment. In numerous embodiments, the scene imager is a video camera. In a variety of embodiments, scene imagers are pointed in an outward facing direction from the patient such that the imager captures images of scenes in front of the patient. In many embodiments, additional sensors are used to augment scene imagers with alternate types of data. For example, GPS coordinates, LIDAR, alternate photosensors, sonar, and/or any other sensor configuration can be used as appropriate to the requirements of specific applications of embodiments of the invention. In some embodiments, scene imagers include at least two cameras located at a fixed distance apart in order to acquire depth information regarding the scene.

External controller 110 is also connected to an eye imager 130 via a communication channel 114. Communication channel 144 is similar to communication channel 112, and enables relatively high-bandwidth communication between the external controller and the eye imager. Eye imagers can be any image capture device capable of accurately recording the motion of an eye. In numerous embodiments, the eye imager is a video camera capable of recording sufficient data as to be used for motion tracking of the eye and/or the point of focus of the eye. This data is collectively described as eye position data, and can include raw image data to be processed by an external controller, and/or processed eye position data depending on the capabilities of the specific implementation of the eye imager architecture. In numerous embodiments, eye position data can further include pupil diameter, eye accommodative state, and/or focal depth. In many embodiments, eye imagers are capable of high-resolution tracking. However, in various embodiments, eye imagers are incapable of measuring small, micro-saccadic eye movements at high frequency. In this case, external controllers and/or eye imagers can measure saccade and add simulated micro-saccades which statistically approximate natural micro-saccadic eye movement. In numerous embodiments, both the scene imager and eye imager are implemented on the same platform as the external controller. For example, in some embodiments, a pair of glasses can be used to house an outward facing scene imager, an inward facing eye imager, and the external controller, as well as any necessary cables and/or transmitters/receivers necessary to implement the communication channels. However, any number of different physical platform configurations can be utilized as appropriate to the requirements of specific applications of embodiments of the invention.

External controller 110 is connected to implanted controller 140 via a communication channel 116. In numerous embodiments, communication channel 116 is a relatively lower-bandwidth communication channel. Due to the low power requirements of the implanted controller, as well as because the implanted controller may be subject to movement due to natural biological movements (e.g. eye movements, muscle movement, etc.), it can sometimes be difficult to establish a high-bandwidth connection that has reliably low latency. In a variety of embodiments, communication channel 116 is implemented using a low-power Bluetooth connection. In numerous embodiments, communication channel 116 is implemented using a near field communication channel, such as, but not limited to, a near-field magnetic induction communication channel, and/or a radio frequency based communication channel and/or ultrasound channel.

Implanted controllers are capable of implementing numerous different artificial sight processes. In many embodiments, implanted controllers are implanted into a patient by mounting the implanted controller onto the exterior of the eye. In some embodiments, the implanted controller is implanted into the episcleral layer of the eye. In a variety of embodiments, the implanted controller is integrated into a contact lens or an intraocular lens. Implanted controllers can obtain dictionaries from external controllers as well as field of view information, and use the received data to continuously select stimulation pulses based on the dictionary. In numerous embodiments, implanted controllers are implemented as an application-specific integrated circuit (ASIC). However, implanted controllers can be implemented using field-programmable gate arrays (FGPAs), or as energy efficient, low-heat general purpose processing devices equipped with machine-readable instruction.

Implanted controller 140 is connected to stimulation interface 150 via a communication channel 142. Communication channel 142 is relatively high-bandwidth and can be implemented using wired or wireless communications methods. In some embodiments, power is transmitted across communication channel 142, or via an alternative power transmission channel. In many embodiments, stimulation interfaces include a dense grid of small electrodes that are surgically connected to the RGC layer of the retina. Where many retinal prosthetics use sparse grids (e.g. 60 electrodes) of large electrodes (e.g. 200 μm), dense electrode grids may have on the order of 1000 electrodes per square millimeter. In some embodiments, the electrodes are placed in a rectangular and/or hexagonal arrangement, where each electrode is between 8 and 15 micrometers in diameter, and each electrode is spaced between approximately 10-50 micrometers apart.

In a variety of embodiments, the electrodes may have diameters of 5-20 μm and spacing of 10-60 μm. In numerous embodiments, the grid is connected to the retina with a semi-regular microwire bundle of approximately the same density as the electrode grid itself. In many embodiments, an interposer device is used to "zoom in" the density of electrodes on the interface to a higher density.

In numerous embodiments, stimulation interfaces include recording circuitry enabling them to record the response of RGCs to electrical stimulation provided by the stimulation interface, and/or their spontaneous electrical activity. These recordings can be used to create the dictionary entries that specify the probability of firing of each RGC in response to a pattern of stimulation. To accomplish this, in some embodiments, the recording circuitry is capable of recording voltages with approximately 10 bits of resolution over a range on the order of hundreds of microvolts, with approximately 10 microvolts of front-end noise, and at a sampling rate of approximately 20 kHz. However, the sensitivity and capabilities of the recording circuitry can be modified, and/or any of a number of different electrode arrangements can be used as appropriate to the requirements of specific applications of embodiments of the invention.

Interfaces can selectively apply variable stimulation to any of the electrodes in the electrode array based on instructions received from the implanted controller. Stimulation pulses can be monophasic, biphasic, triphasic, or multiphasic in time, with amplitude from approximately 0.1-10 pA, and duration of approximately 25-100 psec. In numerous embodiments, interfaces also are capable of recording electrical impulses from adjacent RGCs and transmit the information back to the implanted controller, which in turn can transmit the recorded responses to the external controller. In some embodiments, the implanted controller and the stimulation interface are implemented as part of the same piece of hardware, and therefore the implanted controller is inside the eye itself, rather than internal to the body but on the external face or side of the eye.

External controller 110 is further connected to a network 160 via a communication channel 118 that gives access to a configuration server 170. Communication channel 118 is any communication channel that can be used to access configuration server 170. For example, in numerous embodiments, communication channel 118 is a connection to the Internet, which enables the passage of configuration data from configuration server 170 to the external controller 110. However, any number of different network and communication channel infrastructures can be used to connect the external controller to the configuration server as appropriate to the requirements of specific applications of embodiments of the invention. Configuration servers are used to provide updates to external controllers, eye imagers, or scene imagers as needed. In some embodiments, updates can be provided to implantable controllers as well. Received updates can include, but are not limited to, pre-processed dictionaries, calibration information for any component, or any other information required by the system as appropriate to the requirements of specific applications of embodiments of the invention. In some embodiments, the configuration server generates an initial global dictionary which can be used to generate smaller, faster, and/or more personalized dictionaries. In a variety of embodiments, the configuration server obtains pre-processed dictionaries from other devices. In numerous embodiments, the configuration server utilizes electrical recording and stimulation data to generate dictionaries.

Figure 2:
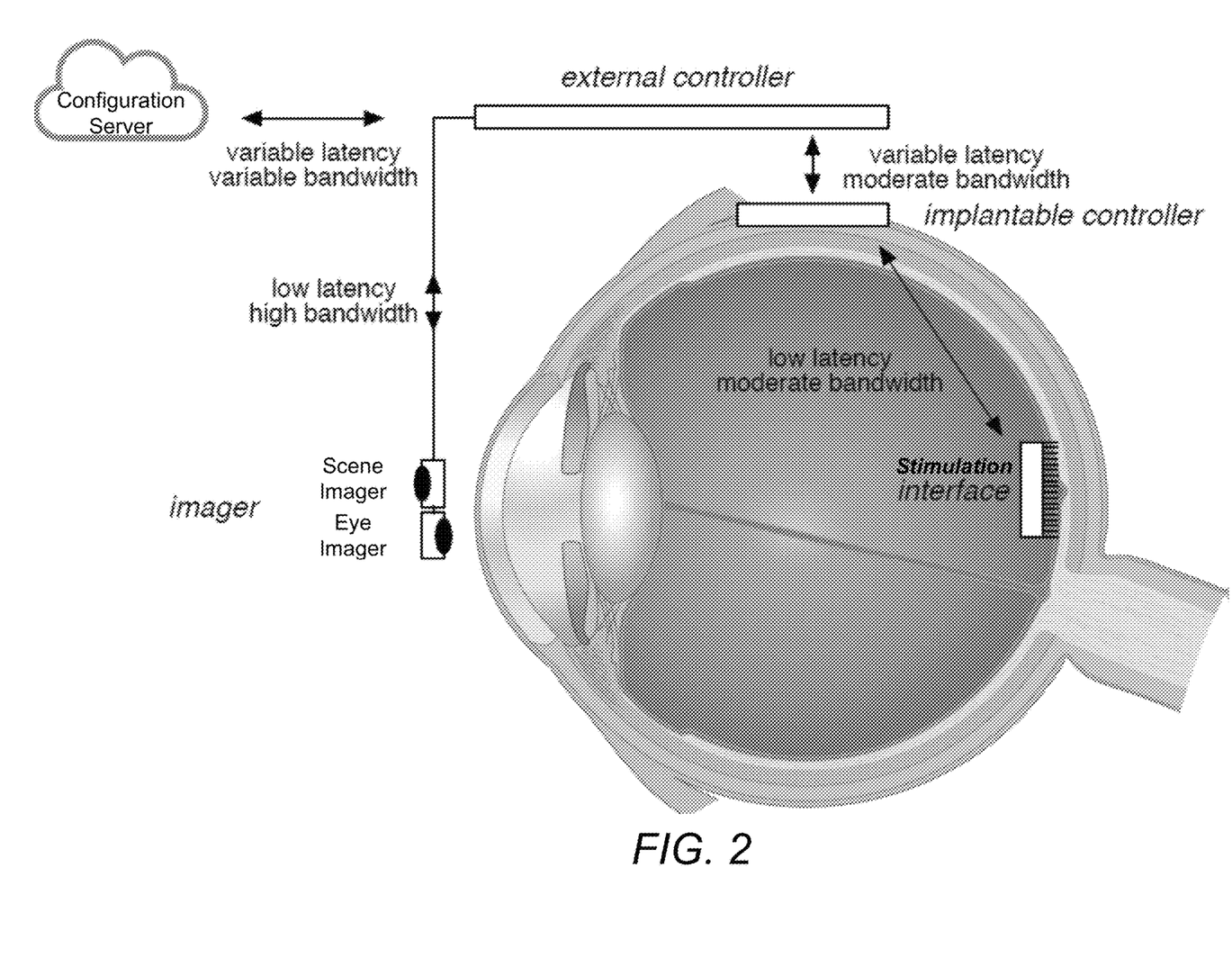
FIG. 2 conceptually illustrates an artificial sight system in accordance with an embodiment of the invention.

While a specific implementation of an artificial sight system in accordance with an embodiment of the invention is illustrated in FIG. 1, any number of different implementations, such as, but not limited to, those that utilize alternate communication methods, can be utilized as appropriate to the requirements of specific applications of embodiments of the invention. For example, an alternative artificial sight system in accordance with an embodiment of the invention is illustrated in FIG. 2. Specific implementations of implanted controllers are discussed below.

Implanted Controllers

Figure 3:
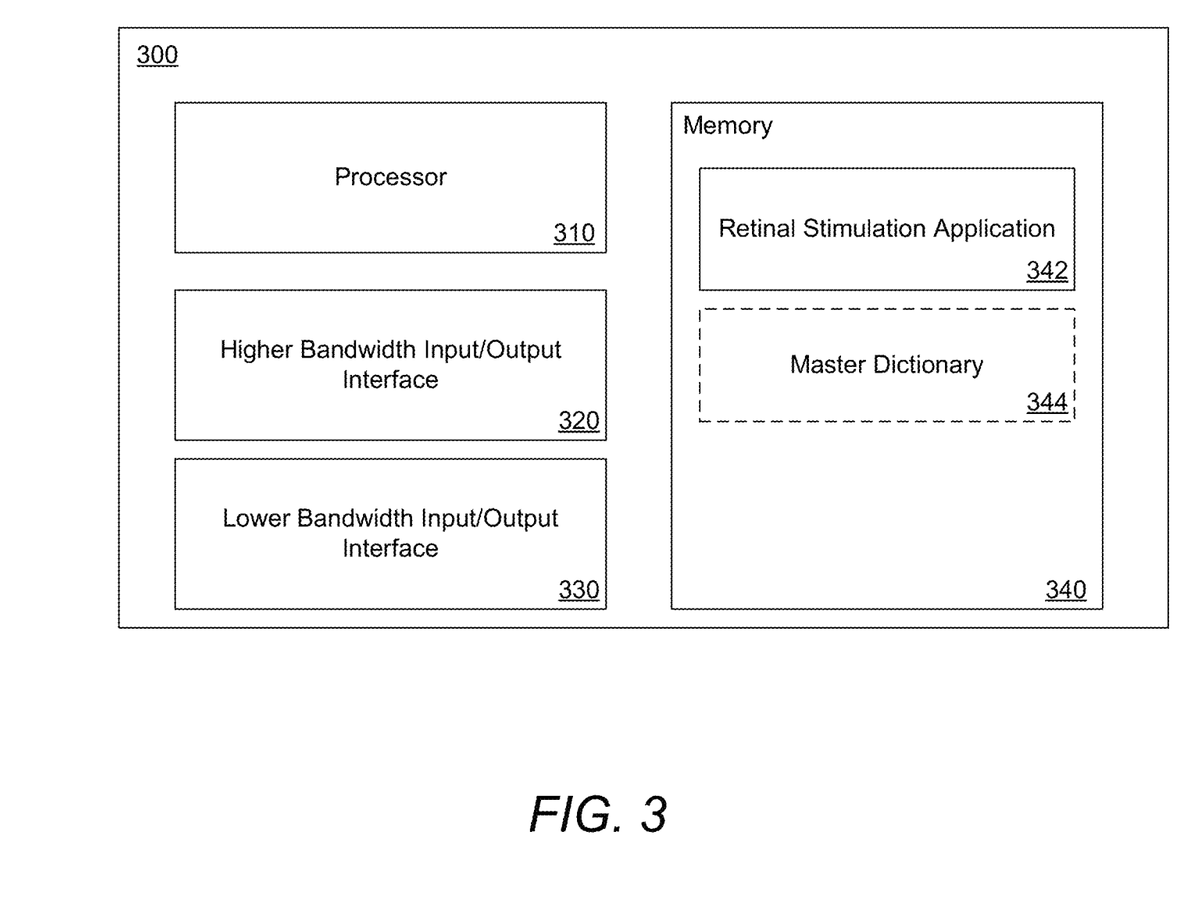
FIG. 3 is a block diagram illustrating an implanted controller of an artificial sight system in accordance with an embodiment of the application.

Implanted controllers are controllers that are implanted into the patient's body abutting or proximal to the eye. Implanted controllers, as discussed above, are able to quickly send instructions to stimulation interfaces based on received dictionaries. Turning now to FIG. 3, a conceptual illustration of an implantable controller in accordance with an embodiment of the invention is illustrated. Implantable controller 300 includes a processor 310. Processer 310 can be any type of processing circuitry capable of implementing logic operations. Implantable controller 300 further includes a higher bandwidth input/output interface 320. The higher bandwidth input/output interface can be used for communicating with other implanted components such as stimulation interfaces. Implantable controller 300 further includes a lower bandwidth input/output interface 330. Lower bandwidth input/output interfaces are used for communicating with external devices, such as external controllers. The terms "higher bandwidth" and "lower bandwidth" reflect relative channel capacities, as currently it is difficult to implement high bandwidth, stable communications to internal devices using communication systems that conform to the power and space requirements associated with processing in and near the human eye. Further, due to eye movements disrupting communication over the channel, latency can be introduced. In many embodiments, the lower bandwidth channel has variable latency which is addressed by the communication systems. However, new communication methods can be integrated into the system which may increase the overall channel capacity and/or reduce latency of the low bandwidth channel, while maintaining the system architecture and methods described herein.

Implanted controller 300 further includes a memory 340. Memory 340 can be implemented using a volatile or non-volatile memory storage method. Memory 340 contains a retinal stimulation application 342 capable of configuring the processor to perform artificial sight processes. In many embodiments, memory 340 contains pre-compiled dictionaries 344 received from the external controller. While a specific implementation of an implanted controller as a general processing device in accordance with an embodiment of the invention is illustrated in FIG. 3, similar processing capabilities can be achieved with specialized circuitry designed to implement pre-determined logic operations similar to those operations described by the retinal stimulation application described, for example, as an ASIC, in order to increase energy efficiency. A description of artificial sight processes is found below.

Artificial Sight Processes

Figure 4:
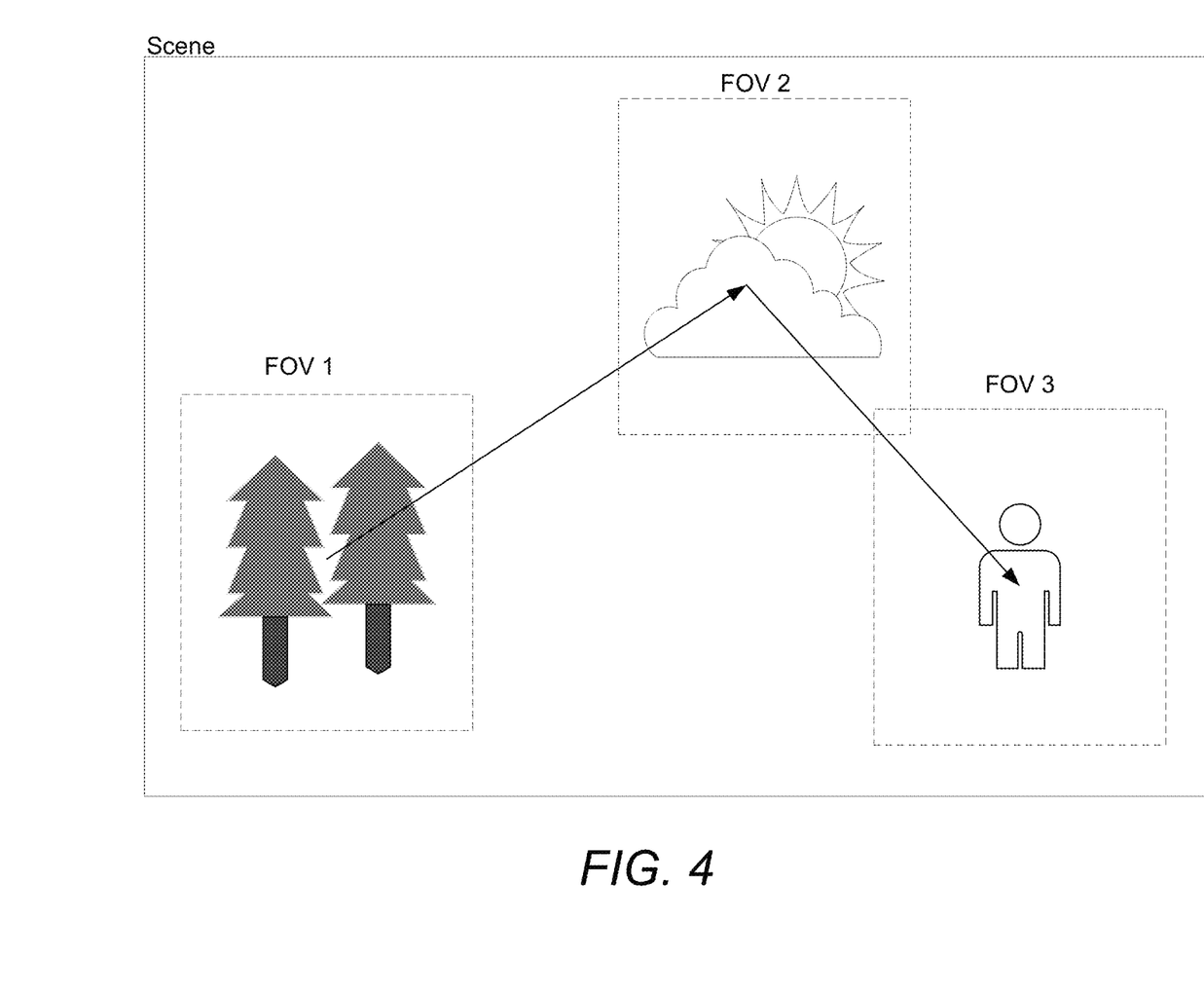
FIG. 4 illustrates a scene broken down into three FOVs based on fixation points in accordance with an embodiment of the invention.

Artificial sight processes can replace the function of degraded neural circuitry by providing electrical stimulation patterns to RGCs that are understood by the patient's brain as coherent, accurate visual stimuli reflecting the surrounding environment. In numerous embodiments, different steps of artificial sight processes are distributed across at least implanted controllers and external controllers. In many embodiments, a master dictionary of stimulation patterns and corresponding evoked neural responses is generated for a user. By rapidly selecting elements from the dictionary based on a field of view (FOV) and providing stimulation to the user's RGCs', neural responses that reflect a desired image can be transmitted to the user's brain, thereby enabling them to "see" the FOV. As used herein, FOV refers to a region of a scene around a fixation point of the viewer which is capable of being rendered by the stimulation interface. An example of an image of a scene and various FOVs as selected by a user's eye movements in accordance with an embodiment of the invention are illustrated in FIG. 4. As the user's eye focuses on different points in the scene, different FOVs can be selected based on the fixation points. Providing the stimulation at a high rate (e.g. approximately 10 kHz), the user's brain will integrate multiple stimulations as arriving at the same time, referred to as "temporal dithering," which enables multiple dictionary elements to be effectively combined to create richer visual sensations. In many embodiments, master dictionaries are generated using a calibration system in a clinical setting.

In a variety of embodiments, master dictionaries contain too many elements be searched quickly enough to achieve temporal dithering. In these cases, the computation can be simplified to reduce computational complexity. For example, the master dictionary can be reduced by removing redundant or infrequently used elements and/or the master dictionary can broken into individual FOV dictionaries that are designed for evoking a particular set of neural responses corresponding to a particular FOV. In many embodiments, external controllers can be provided the master dictionary for the particular patient, and/or can generate FOV dictionaries of the master dictionary by selecting entries that are appropriate and useful for the current FOV of the patient. In many embodiments, the stimulation interface does not cover every RGC, and therefore the FOV may be considerably smaller than the size of the image captured by the scene imager. These smaller dictionaries can increase the efficiency of the system by reducing the time to loop over dictionary entries and determine the next entry to use during a given stimulation period, typically using a "greedy" or a dynamic programming approach. Further, to provide additional computational complexity reduction, the resolution of the target image can be reduced, and/or computations can be split over multiple controllers. Processes for generating master dictionaries are described below.

A. Master Dictionaries

A master dictionary can be generated by providing stimulation through a particular electrode in a stimulation interface, recording neural activity using the stimulation interface, calibrating the neural activity, and obtaining from this calibration the probability of spiking by each RGC that is recorded. This probability can constitute a single dictionary entry. Given that there can be a dictionary entry for every possible current level through each electrode in the stimulation interface and all combinations thereof, there may not be sufficient time to generate all possible entries for a particular patient. However, with sufficient dictionary entries, performance of the system is not, or minimally, impeded.

Figure 5:
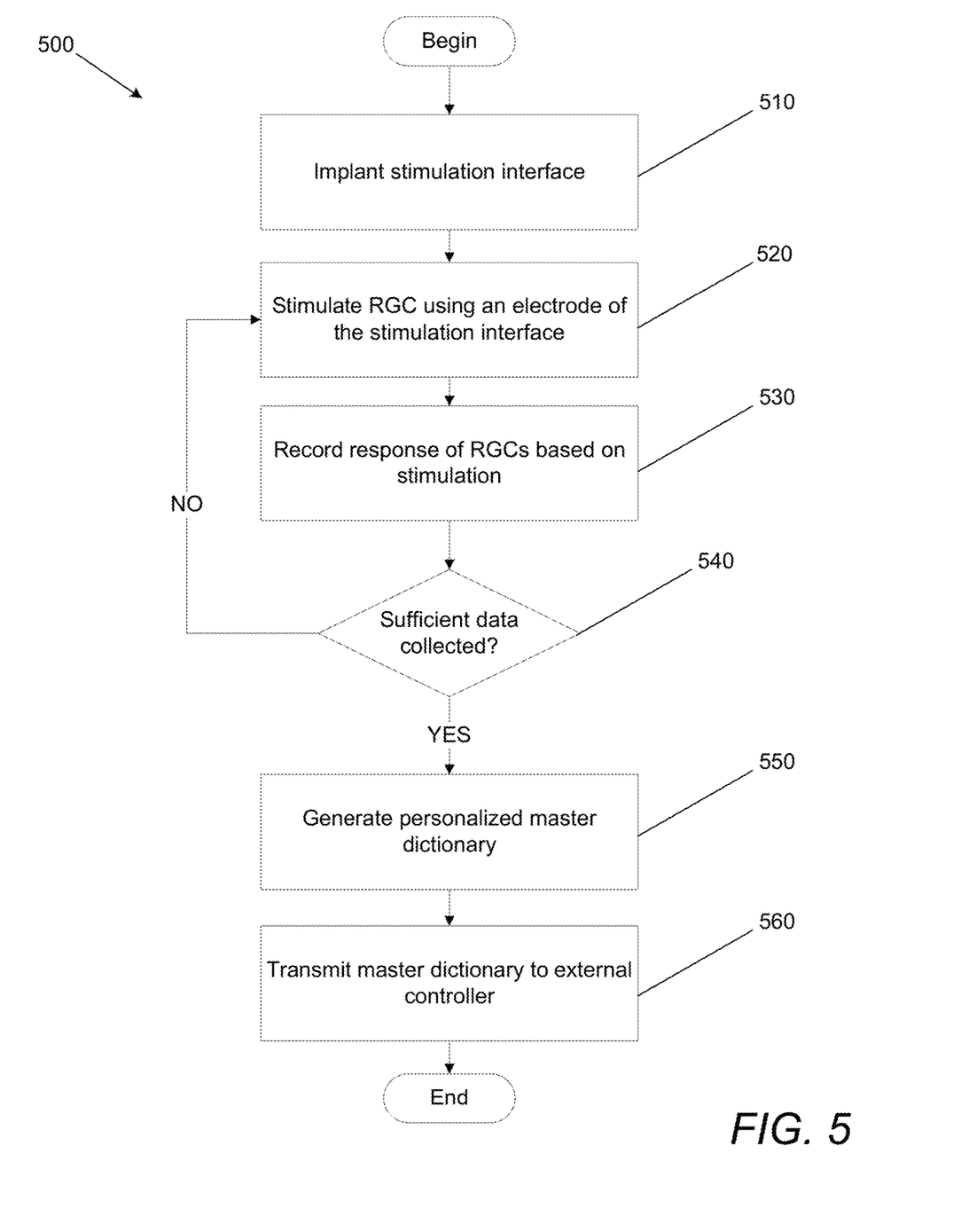
FIG. 5 is a flow chart illustrating an artificial sight process for generating master dictionaries in accordance with an embodiment of the invention.

Turning now to FIG. 5, a process for generating personalized master dictionaries in accordance with an embodiment of the invention is illustrated. Process 500 includes implanting (510) a stimulation interface. In many embodiments, the stimulation interface has already been implanted. Process 500 further includes stimulating (520) RGCs using at least one electrode of the stimulation interface. Responses to the stimulus from RGCs nearby the stimulating electrode can be recorded using electrodes in the stimulation interface. If a sufficient number of responses has been collected (540), a personalized master dictionary based on the recorded responses can be generated (550). In many embodiments, the master dictionary is a data structure that stores the expected response to a particular stimulus pattern. If an insufficient amount of data has been collected (540), additional stimuli can be performed and additional responses can be recorded. Once generated, the master dictionary can be transferred (560) to an external controller.

In some embodiments, the master dictionary and/or dictionaries (e.g. sub-dictionaries discussed below as "dictionaries") can be pruned. In various embodiments, a smaller version of the master dictionary is computed that works across many natural images. For example, by selecting the most frequently used electrodes across a battery of many common targets, a workable reduced master dictionary can be generated. The number of elements selected for the reduced master dictionary can be based on a tunable threshold value based on performance, computational availability, the common scenes for a particular patient, and/or any other metric as appropriate to the requirements of specific applications of embodiments of the invention.

B. Selecting Dictionary Elements for Stimulation

Figure 6:
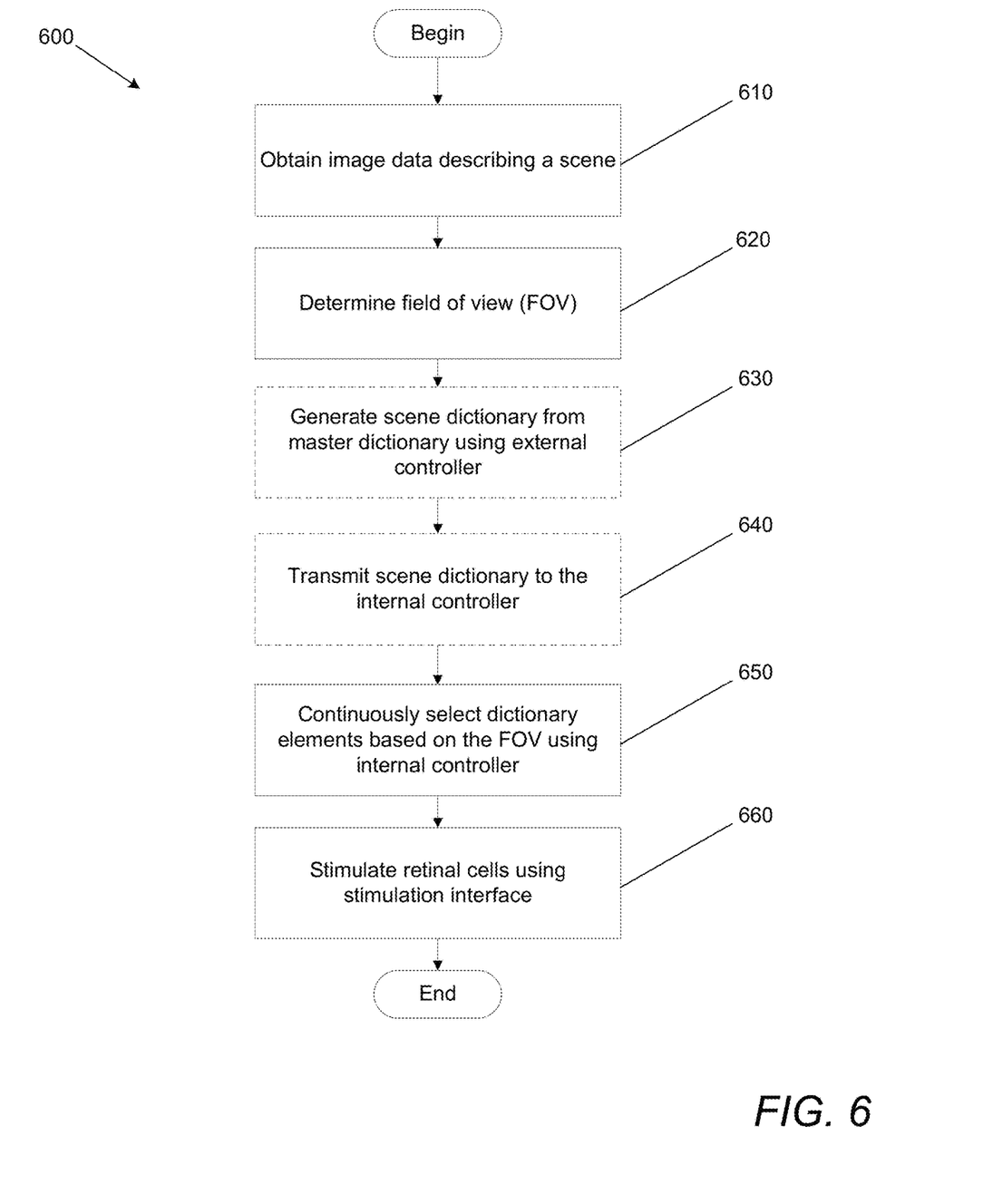
FIG. 6 is a flow chart illustrating an artificial sight process for selecting dictionary elements for stimulating retinal cells in accordance with an embodiment of the invention.

Elements from a dictionary can be selected to visualize a particular FOV. Sight can be restored by enabling a user to view what they are "looking" at by artificially capturing the scene in front of them (or any arbitrary scene) and choosing the dictionary elements to recreate the neural responses that would have been generated by a healthy eye. Turning now to FIG. 6, a process for selecting dictionary elements for stimulation in accordance with an embodiment of the invention is illustrated.

Process 600 includes obtaining (610) image data describing a scene. Image data can be obtained from scene imagers. An FOV is determined (620) from the scene based on the gaze of the user. In numerous embodiments, the gaze of the user can be determined using the eye position data from the eye imager and any gaze tracking process. In numerous embodiments, the FOV is based on the amount of the scene around the fixation point of the user that can successfully be converted into electrical stimulation by a stimulation interface. A single image can have multiple FOVs based on the range of the user's eye movements. In some embodiments, different FOVs are identified in the same scene.

In some embodiments, the eye imager cannot record the eye-position at a very high accuracy to measure microsaccades. In this case, simulated microsaccades can be sampled with statistics that match the statistics of microsaccades in healthy patients but not necessarily the exact underlying trajectory. The FOV can be moved around the recorded eye location with these simulated microsaccades. In other embodiments, a similar strategy can be applied for other kinds of eye-movements such as jitter, which is also hard to measure. In other embodiments, the simulated eye-movements can be chosen to simultaneously obey the statistics of eye-movements in healthy patients and make the resulting FOV easy to reproduce in a prosthesis.

As noted above, in many embodiments, a master dictionary can be reduced in size to sufficiently achieve temporal dithering. However, in many embodiments, FOV dictionaries are used to achieve additional performance. In these situations, a FOV dictionary can be generated (630) from a master dictionary using the external controller. To create a FOV dictionary, the degree of matching between a stimulus and the desired response (e.g. "seeing" the FOV) can be calculated using the following notations and assumptions:

Notations

S: target visual stimulus (dimensions: #pixels×1), where S is a static frame of the visual stimulus (FOV)

R: neural responses (dimensions #cells×1)

f(S,R) is the Utility Function reflecting degree of matching between S and R

A: Reconstruction matrix (dimensions #pixels×#cells). Columns of A correspond to the reconstruction filters of different cells.

M: responses to artificial stimulation $D = \{(e_d, a_d, p_d)\}_{d=1}^{d=|D|}$. stimulation dictionary, where each element d consists of stimulation electrodes ($e_d$), current amplitudes ($p_d$), and response probability vector ($p_d \in [0,1]^{\#cells \times 1}$). Response for cell i, $R_d^i \sim$ Bernoulli ($p_d^i$) when current pattern d is stimulated.

Assumptions

A dynamic stimulus can be approximated with a sequence of static frames.

A sequence of retinal responses, produced in rapid succession by electrical stimulation, is summed by the brain to produce a single perceived image. Therefore, the reconstructed stimulus for the sequence $R_1, \ldots, R_T$, is given by $R = \Sigma_{t=1}^{t=T} R_T$ Responses generated by a stimulation pattern, $d_t$, are independent of the responses to the previous stimulation patterns, $d_1, \ldots, d_{t-1}$, as long as no stimulus is delivered to a cell during its spiking refractory period.

In general, a well selected stimulation pattern is one which has a high degree of matching between stimulus S and neural response R, given by f(S,R). f(S,R) can be calculated in any number of ways depending on the requirements of a specific applications of an embodiment of the invention. In the response space, f(S,R) can be calculated as f(S, R)= σ(h(S), R), where σ is a notation of similarity between responses and h(S) is an encoding model that predicts neural responses for a given stimulus. In various embodiments, σ can be calculated using an indicator function, Hamming distance, Victor-Purpura distance, deep learning methods using neural data, and/or any other method as appropriate to the requirements of specific applications of embodiments of the invention. Further, h(S) can be a linear/non-linear Poisson model, a generalized linear model, encoding models with spatial nonlinearities and adaptation, deep learning models, and/or any other model as appropriate to the requirements of specific applications of embodiments of the invention.

In the stimulus space, f(S,R) can be calculated as $f(S,R) = \rho(S, g(R))$, where ρ is a notation of similarity between stimuli, and g(R) is a decoding model that predicts how a brain might interpret the neural responses. In numerous embodiments, ρ is calculated as negative mean-squared error (MSE): $\rho(S, \hat{S}) = -\|S - \hat{S}\|2/2$. The perceived visual image can be approximated by linearly reconstructing neural responses: $g(R) = \hat{S} = AR$, with A an optimal linear filter. In various embodiments, ρ is calculated as a structural similarity index (SSIM), or another measure of perceptual similarity of images as appropriate to the requirements of specific applications of embodiments of the invention. In numerous embodiments, ρ can be calculated based on a particular task, for example, when walking on a street, the similarity of edges that indicate pavement can be measured. g(R) can be calculated using an inverted encoding model or a neural network. In various embodiments g(R) can be calculated using an optimal linear filter. However, any number of different methods of calculating ρ and g(R) can be used as appropriate to the requirements of specific applications of embodiments of the invention. Further, when the stimulus or response space is not known, f(S,R) can be calculated as $f(S,R) = G\langle m(S), n(R) \rangle$, where the visual stimulus is transformed to the latent space by m(.), neural responses are transformed to the latent space by n(.), and <.,.> is the inner product in Euclidean space.

A FOV dictionary can then be generated by selecting a number of elements from the master dictionary that best fit the FOV. In order to select the elements, the number of times each element of the master dictionary that could be used in the FOV can be counted. For example, let q be a vector of the number of times each dictionary element is called; D be a matrix (# cells×# dictionary elements), where each column is the probability of stimulation of different cells for the corresponding dictionary element; Dq the expected responses; and B the desired size of the FOV dictionary, then: $q^* = \max f(S, Dq)$; with $q \geq 0$; $\Sigma_i q_i \leq B$. The FOV dictionary can then be given by all stimulation elements which have a non-zero entry in q*. Once generated, the FOV dictionary can be transmitted (640) to the internal controller.

The internal controller then continuously selects (650) dictionary elements based on the FOV of the user. Given the size of the stimulation interface, it may not be possible to recreate an entire FOV. Indeed, the scene imager itself may have a larger field of view that the user. Based on the gaze of the user, an FOV is selected for reproduction, and the dictionary elements selected recreate that portion of the scene. In numerous embodiments, the internal controller stores the master dictionary or reduced master dictionary. In various embodiments, the internal controller instead stores a FOV dictionary. However, in many embodiments, the internal controller can store more than one type of dictionary. The problem of which dictionary elements to select reduces to choosing a sequence of dictionary elements for stimulation $d_1, \ldots, d_T$ in a way that temporal dithering can be exploited to provide multiple independent stimulations within a single biological integration window to trigger a perception of the FOV. Generally, this can be formalized as:

$$d_1, d_2, \ldots, d_T = \text{argmax } E_{R_i \sim M(d_i)} f\left(S, \sum_{i=1}^{T} R_i\right)$$

where E is an expected value function.

One approach to solving the above problem is with a "greedy" algorithm, which can be formalized as:

$$P_t \triangleq P_{t-1} + R_t$$

$$d_{t+1} = \text{argmax } f(S, P_t + R_{t+1}), \text{ where } R_t \sim M(d_t)$$

The above equation can be implemented in any number of ways depending on the utility function selected to be maximized. For example, when the utility function is selected to negative MSE, and g(R)=AR, a simulation choice at time step t is given by:

$$d_t = \operatorname{argmin}_{d \in \mathcal{D}} \mathbb{E} \left\| S - A \left( \sum_{l=1}^{l=t-1} R_l + R_d \right) \right\|_2^2$$

Where the expectation is over $R_1, \ldots, R_{t-1}$, the responses elicited in previous time steps (with $R_l \sim \text{Bernoulli}(p_{d_l})$ $\forall l \in \{0, \ldots, t-1\}$). For the choices of linear reconstruction and mean-squared error, the greedy algorithm can be implemented by decomposing the objective function value into its bias and variance components. Because the response at each time step is assumed to be independent of preceding responses, the total variance decomposes as the sum of the variance in all time steps:

$$\mathbb{E} \left\| S - A \left( \sum_{l=1}^{l=t-1} R_l + R_d \right) \right\|_2^2 =$$

$$\left\| S - \mathbb{E} \left[ A \left( \sum_{l=1}^{l=t-1} R_l + R_d \right) \right] \right\|_2^2 + \sum_{i \in \text{pixels}} \text{var} \left( A_i \left( \sum_{l=1}^{l=t-1} R_l + R_d \right) \right) =$$

$$\left\| S - (\tilde{S}_{t-1} + A p_d) \right\|_2^2 + v_d + \hat{V}_{t-1}$$

where $A_i$ is the ith row of A; and $p_{d_t}$ and $v_d$ are the contribution to mean and variance in perception for the dth dictionary element;

$$\hat{S}_t(= \hat{S}_{t-1} + A_{p_{d_t}})$$

and $V_t(=\hat{V}_{t-1} + v_{d_t})$ are the cumulative mean and variance in perception due to stimulation patterns chose in time steps $\{1, \ldots, t\}$. To satisfy the independence assumption, stimulating a cell during its refractory period is generally avoided. To accomplish this, dictionaries generated using the greedy algorithm can be restricted to stimulation patterns that do not activate cells that were already targeted in the preceding 5 ms. In some embodiments, the window is between 1 ms and 10 ms. In numerous embodiments, generated dictionary elements that are determined to have low value are discarded.

However, in numerous embodiments, instead of utilizing a greedy algorithm, a dynamic programming approach can be taken in order to solve for multiple steps at a time. For example, in order to calculate k-steps ahead, assume stimulation at time step t, then T(k, d) ≜ the best utility for a stimulation sequence that ends at time step t+k, and stimulation d; and P(k, d) ≜ the cumulative responses ($\Sigma_{t=1}^{t=t+k} R_t$). The induction step can then be calculated as:

$$T(k, d) = \max_{d'} E f(S, P(k-1, d') + R_d)$$

$$P(k, d) = \max_{d'} [P(k-1, d') + R_d]$$

After iterating up to step k=K, choose the K-step stimulation sequence that attains $\max_d T(K, d)$. This can be quickly looked up by keeping track of the maximizing d' for each d and step k. However, as one of ordinary skill in the art can appreciate, any number of different methods can be used to resolve $d_1, d_2, \ldots, d_T = \operatorname{argmax} E_{R_i \sim M(d_i)} f(S, \Sigma_{i=1}^T R_i)$ as appropriate to the requirements of specific applications of an embodiment of the invention.

In numerous embodiments, at every time step of approximately 10 kHz, an appropriate electrical stimulation pattern is selected from the dictionary. In many embodiments, dictionary elements (electrical stimulation patterns) are selected at each time step (roughly 0.1 ms), and that element is selected from the currently used dictionary. The element selected is the most effective for visual perception among the choices in the dictionary (see equations above). This is a form of temporal dithering because the biological visual system integrates information over much longer time scales (e.g. 10-100 ms) and therefore many stimulation patterns (dictionary elements) can be presented and summed to produce a perceived image in the patient.

This process can result in an "unlocked frame rate" of between approximately 10 and 240 Hz. In numerous embodiments, the temporal dithering of the stimulation is on the order of 10-100 kHz. By rapidly selecting dictionary elements and summing the corresponding stimulation, patients can see in much higher fidelity in real time. In numerous embodiments, this also means that the vast number of possible stimulation patterns do not need to be fully explored during calibration (e.g. when time constraints may be present due to having the patient in a clinic). For example, with 1000 electrodes and 100 current levels on each electrode, the number of possible dictionary elements is $100^{1000}$, which would be currently infeasible and/or impractical given the computation and storage requirements. However, with temporal dithering as described herein, calibration using just 100*1,000=100,000 entries is achievable, and this dictionary combined with temporal dithering can be used to capture a large fraction of the possible images that a patient can see. The selected dictionary elements can be used to stimulate (660) RGCs using a stimulation interface to give the impression of vision of the FOV.

Figure 7:
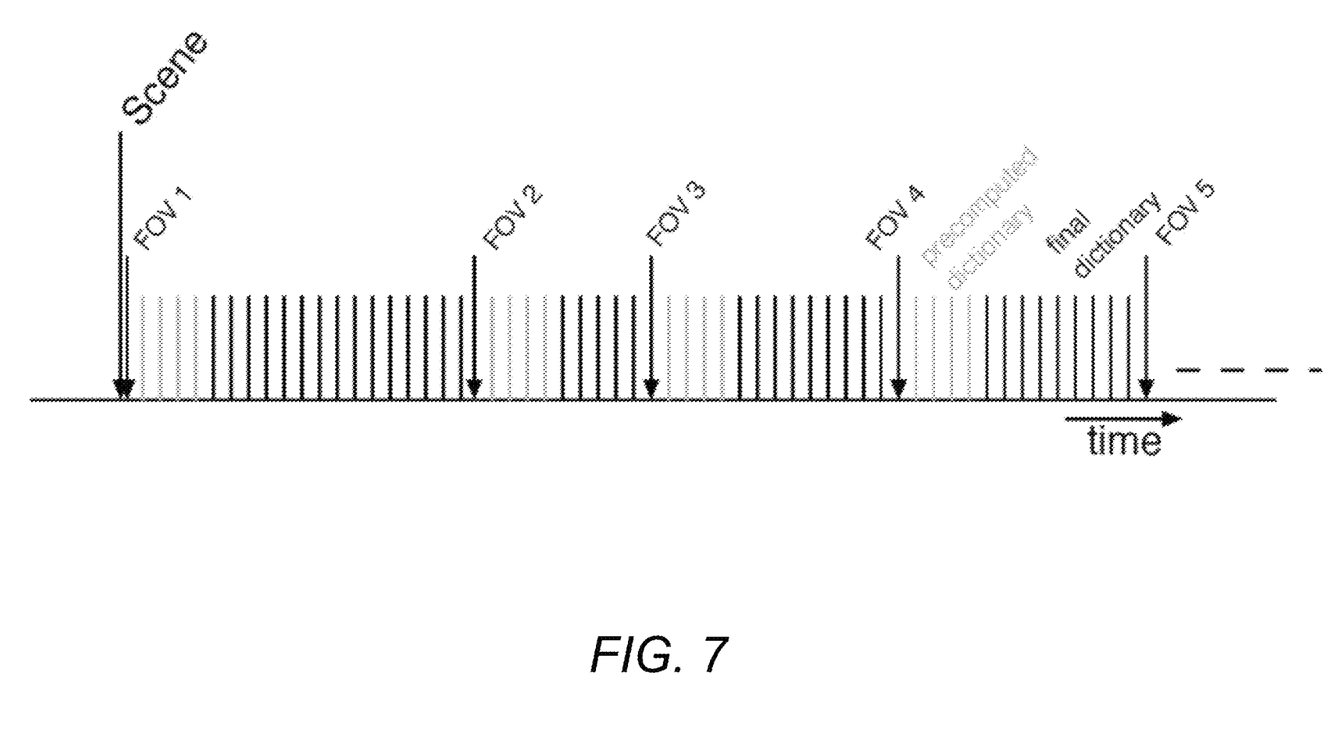
FIG. 7 is a chart illustrating a timeline of events during an artificial sight process in accordance with an embodiment of the invention.

As noted above, scenes can be subdivided into multiple FOVs depending on the gaze of the user. However, in some embodiments, for some scenes, generation of a FOV dictionary can cause lag. That is, the FOV dictionary is not ready in time to reproduce smooth vision. During this delay, the implanted controller can utilize a stored, precomputed dictionary corresponding to a precomputed target with closest location to recorded FOV and/or a generic match for the FOV (e.g. a neutral, uniform head model instead of a person in the FOV). After the external controller generates the more accurate dictionary, it can be sent to the implanted controller to continue the stimulation and fine-tune visual perception. A timeline illustrating the above concept in accordance with an embodiment of the invention is illustrated in FIG. 7. In many embodiments, for every new scene, there are multiple eye movements, each lasting for a variable duration. For each eye-movement, there will be a sequence of stimulation patterns delivered from the dictionary, in rapid sequence (e.g. 10 kHz). In some embodiments, there are two stages of stimulation. In the first stage, stimulation can initially be performed from a precomputed dictionary that is not ideal, while a more accurate FOV dictionary is computed. In the second stage, the stimulations can be performed from the more accurate dictionaries.

Precomputed dictionaries used during the period that the correct dictionary for the FOV is being determined can be selected based on an approximate FOV, and can rely on a low-resolution version of the approximate image. This is analogous to transmitting low spatial frequency image information initially, and then later transmitting the high spatial frequency information to complete the image, in compression schemes such as JPEG.

Figure 8:
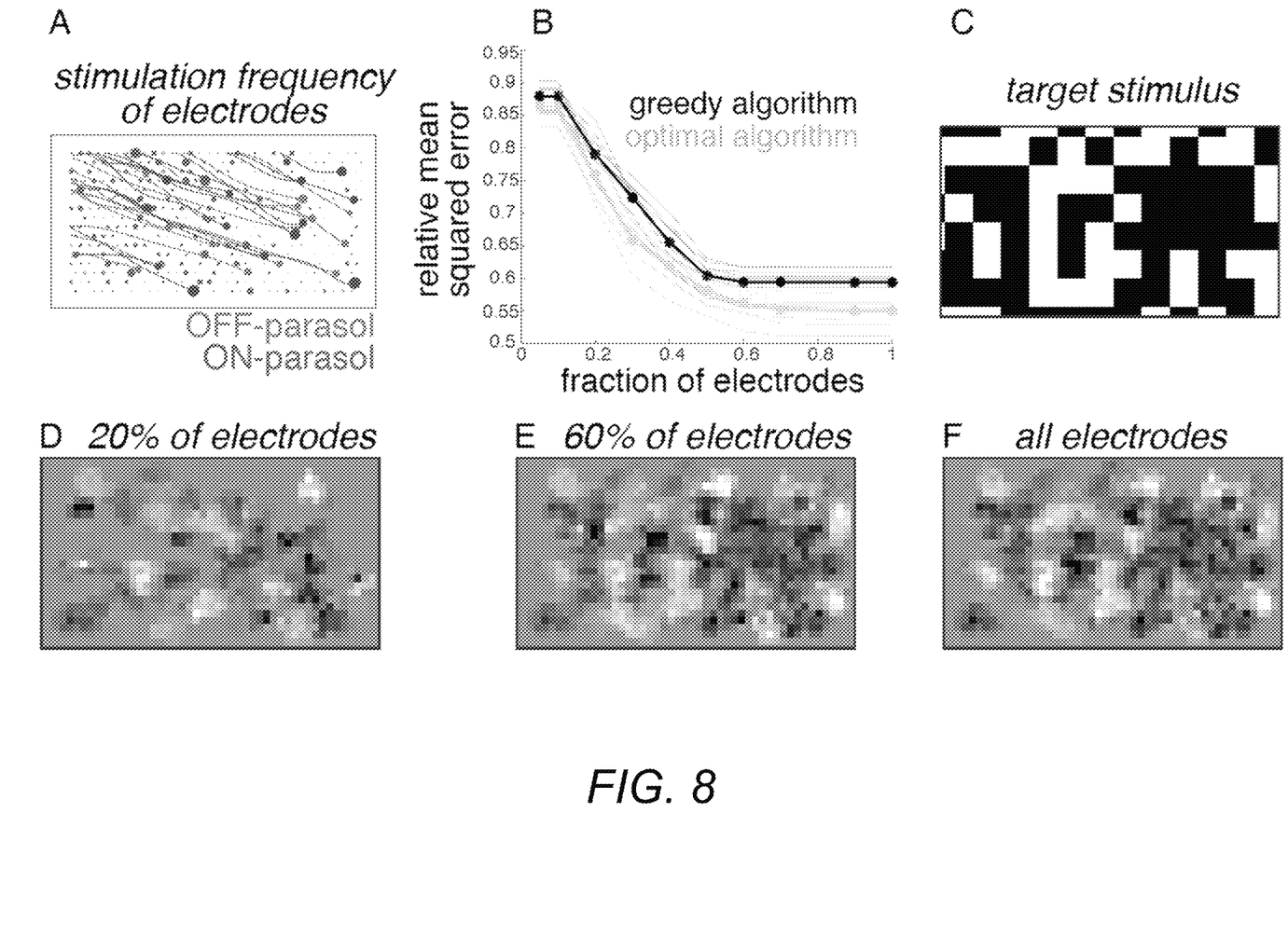
FIG. 8 illustrates six charts demonstrating a stimulation frequency of electrodes, the performance of a greedy algorithm as compared to an optimal algorithm, a sample target stimulus, and the varying fidelity of artificial sight given activation of different amounts of electrodes in accordance with an embodiment of the invention.

Turning now to FIG. 8, exemplary data in accordance with an embodiment of the invention is illustrated. Chart A illustrates the frequency of stimulating different electrodes (size of circles), overlaid with axons (lines) and somas (colored circles) inferred from electrophysiological imaging. Chart B illustrates reconstruction error as a function of the fraction of electrodes included in the dictionary for multiple targets and averaged over 20 targets (top, thick line), the lower bound on error of any algorithm for the subsampled dictionaries for individual targets and averaged across targets (bottom, thick line). Chart C illustrates a target stimulus. Charts D-F illustrate reconstruction using the dictionary with most frequently used 20%, 60% and 100% of electrodes, respectively.

The results indicate that efficient hardware can be designed by limiting stimulation to the most frequently stimulated electrodes. For example, in many embodiments, an artificial sight process includes evaluating which electrodes are most useful, and ignoring the electrodes that are not, thus cleaning out many entries the master dictionary, and therefore entries in FOV dictionaries, to increase downstream efficiency. In many embodiments, at least 50% of electrodes can be ignored out at the start, thus permanently shrinking the dictionary.

Across multiple target images, the distribution of stimulated electrodes was spatially non-uniform. More frequently chosen electrodes had larger number of axons nearby (Chart A). These electrodes typically stimulated multiple cells simultaneously, indicating that the algorithm exploits non-selective stimulation patterns. This suggests that previous approaches to optimal stimulation based on maximizing selectivity are not always the most effective. To understand if this finding can guide efficient hardware design, the dictionary was restricted to the most frequently chosen electrodes. The greedy algorithm was applied with the reduced dictionary, and reconstruction error was averaged across 20 random targets. A minimal increase in error was observed even after reducing the number of available electrodes by 50%. On reducing the number of available electrodes further, the error increased gradually. This increase was not due to the greedy stimulation choices, as a lower bound for the best algorithm showed similar behavior (Chart B, lower curve). These results suggest that, as noted above, an efficient device could maintain a reduced dictionary in which approximately 50% of the stimulating units are turned off, reducing memory access and static power. Note that all stimulating units are required during the initial calibration phase to select the most frequently used subset of electrodes.

While the above processes have been described with specific respect to sight, the same processes could be applied to any of the different senses. For example, in numerous embodiments, instead of a visual stimulus, an auditory, olfactory, or somatosensory stimulus in a system connected to neurons associated with the respective sense. Further, the above processes are not restricted to operation on individual cell spiking. In many embodiments, neural responses are measured as aggregate activity of large populations such as, but not limited to, EEG recordings, LFP recordings, ECOG recordings, optical recordings, and/or any other neural response recording method as appropriate to the requirements of specific applications of embodiments of the invention. Additionally, in a variety of embodiments, the stimulation need not be electrical in nature. Indeed, any number of neural stimulation methods can be used such as, but not limited to, optical magnetic, sonic, and/or any other neural stimulation method that can be used to stimulate neurons. One of ordinary skill in the art can appreciate that the described temporal dithering methods can be utilized in any of a number of different ways using a variety of application specific inputs without departing from the scope or spirit of the invention.

Although specific systems and methods for artificial vision are discussed above, many different modifications can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

The invention claimed is:

1. A retinal prosthesis system comprising:
an external controller;
a scene imager in communication with the external controller;
an eye imager in communication with the external controller;
an implanted controller in communication with the external controller via a first communication channel; and
a stimulation interface in communication with the implanted controller via a second communication channel, where the stimulation interface is positioned to stimulate a plurality of retinal ganglion cells (RGCs) of the eye, and the stimulation interface comprises a dense electrode grid;
where the external controller is configured to:
obtain image data describing a scene from the scene imager;
obtain eye position data from the eye imager;
determine a field of view (FOV) in the scene based on the eye position data; and
transmit the FOV to the implanted controller;
where the implanted controller is configured to:
obtain the FOV from the external controller;
continuously select stimulation pulses from a dictionary based on the FOV; and
stimulate the plurality of RGCs using the stimulation interface in accordance with the selected stimulation pulses.

2. The system of claim 1, wherein the stimulation of the RGCs is performed at between 10 kHz to 100 kHz.

3. The system of claim 1, wherein the dictionary is a master dictionary; and the external controller is further configured to transmit the master dictionary to the implanted controller.

4. The system of claim 3, wherein to compile the master dictionary, the external controller is configured to:
stimulate the plurality of RGCs using the stimulation interface via the implanted controller;
record responses of the plurality of RGCs based on the stimulation using the stimulation interface, via the implanted controller; and
generate a set of dictionary elements indicating neural activity in response to specific stimulation provided by the stimulation interface.

5. The system of claim 3, wherein the master dictionary is a reduced master dictionary.

6. The system of claim 1, wherein:
the dictionary is a FOV dictionary;
wherein to compile the FOV dictionary, the external controller is configured to select elements from a master dictionary which are most relevant to the FOV; and
the external controller is further configured to transmit the FOV dictionary to the implanted controller.

7. The system of claim 6, wherein to select elements from the master dictionary, the external controller is configured to:
calculate a vector $q^*=\max f(S,Dq)$; with $q \geq 0$; $\Sigma_i q_i \leq B$; and
selecting dictionary elements of $q^*$ which are non-zero.

8. The system of claim 6, wherein the implanted controller is further configured to use a precompiled dictionary in an interim period between receiving the FOV and receiving the FOV dictionary.

9. The system of claim 1, wherein the first communication channel is a wireless communication channel utilizing a near-field magnetic communication technology.

10. The system of claim 1, wherein the first communication channel is a wireless communication channel utilizing a radio frequency communication technology conforming to the Bluetooth standard.

11. The system of claim 1, wherein the second communication channel is a wired communication channel configured to power the dense electrode grid.

12. The system of claim 1, wherein the second communication channel is a wireless communication channel.

13. The system of claim 1, wherein stimulation of the plurality of RGCs occurs with sufficient speed to trigger the temporal dithering effect.

14. The system of claim 1, wherein to select stimulation pulses from the dictionary and the FOV, the implanted controller is further configured to utilize a greedy algorithm.

15. The system of claim 1, wherein to select stimulation pulses from the dictionary and the FOV, the implanted controller is further configured to utilize a dynamic programming algorithm.

16. The system of claim 1, wherein the implanted controller is configured to be implanted in the episcleral layer of an eye.

17. The system of claim 1, wherein the implanted controller is incorporated into a contact lens.

18. A method for providing artificial sight, comprising:
obtaining image data describing a scene from a scene imager;
obtaining eye position data from an eye imager;
determining a field of view (FOV) in the scene based on the eye position data using a retinal prosthesis;
continuously selecting stimulation pulses from a dictionary and the FOV using the retinal prosthesis; and
stimulating a plurality of retinal ganglion cells using a stimulation interface of the retinal prosthesis in accordance with the selected stimulation pulses.

19. The method of claim 18, wherein the dictionary is a FOV dictionary which is compiled by selecting elements from a master dictionary which are most relevant to the FOV.

20. The method of claim 16, wherein selecting stimulation pulses from the dictionary based on the FOV is achieved using a greedy algorithm.

* * * * *